(12) United States Patent
Liu et al.

(10) Patent No.: US 6,610,089 B1
(45) Date of Patent: Aug. 26, 2003

(54) SPINAL IMPLANT AND CUTTING TOOL PREPARATION ACCESSORY FOR MOUNTING THE IMPLANT

(75) Inventors: Mingyan Liu, Bourge La Reine (FR); Daniel Chopin, Groffliers (FR); Hans-Jörg Meisel, Berlin Lichterfelde (DE)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/420,622

(22) Filed: Oct. 19, 1999

Related U.S. Application Data

(63) Continuation-in-part of application No. PCT/IB98/01324, filed on Aug. 25, 1998.

(30) Foreign Application Priority Data

Aug. 26, 1997 (FR) .............................. 97 10664

(51) Int. Cl.$^7$ ................................. A61F 2/44
(52) U.S. Cl. ................. 623/17.11; 623/16.11
(58) Field of Search .......... 623/17.11–17.16, 623/16.11

(56) References Cited

U.S. PATENT DOCUMENTS

| | | | |
|---|---|---|---|
| 4,349,921 A | 9/1982 | Kuntz ................... 3/1 |
| 4,834,757 A | * 5/1989 | Brantigan ............. 623/17 |
| 4,936,848 A | 6/1990 | Bagby .................. 623/17 |
| 5,015,247 A | 5/1991 | Michelson ............. 606/61 |
| 5,062,845 A | 11/1991 | Kuslich et al. ........ 606/80 |
| 5,190,548 A | 3/1993 | Davis ................... 606/80 |
| 5,250,061 A | 10/1993 | Michelson ........... 606/160 |
| 5,304,191 A | 4/1994 | Gosselin ............. 606/172 |
| 5,306,309 A | 4/1994 | Wagner et al. ........ 623/17 |
| 5,425,772 A | 6/1995 | Brantigan ............. 623/17 |
| 5,443,514 A | 8/1995 | Steffee ................ 623/17 |
| 5,445,639 A | 8/1995 | Kuslich et al. ........ 606/80 |
| 5,458,638 A | 10/1995 | Kuslich et al. ....... 623/17 |
| 5,484,437 A | 1/1996 | Michelson ............ 606/61 |
| 5,499,984 A | 3/1996 | Steiner et al. ........ 606/80 |
| 5,607,424 A | 3/1997 | Tropiano .............. 606/61 |
| 5,609,635 A | 3/1997 | Michelson ........... 623/17 |
| 5,609,636 A | 3/1997 | Kohrs et al. ......... 623/17 |
| 5,669,909 A | 9/1997 | Zdeblick et al. ...... 606/61 |
| 5,683,463 A | 11/1997 | Godefroy et al. ..... 623/17 |
| 5,720,749 A | 2/1998 | Rupp .................. 606/79 |
| 5,766,252 A | 6/1998 | Henry et al. ......... 623/17 |
| 5,782,830 A | 7/1998 | Farris ................. 606/61 |

(List continued on next page.)

FOREIGN PATENT DOCUMENTS

| | | | | |
|---|---|---|---|---|
| DE | WO 97/06753 | * | 2/1997 | ......... A61F/2/44 |
| EP | 0493698 B1 | | 7/1992 | |
| EP | 0637440 A1 | | 2/1995 | |
| EP | 0646366 A1 | | 4/1995 | |
| EP | 0 834 295 A1 | | 4/1998 | |

(List continued on next page.)

Primary Examiner—Corrine McDermott
Assistant Examiner—Thomas Barrett
(74) Attorney, Agent, or Firm—Woodard, Emhardt, Moriarty, McNett & Henry LLP

(57) ABSTRACT

This invention relates to a spinal implant for promoting fusion of adjacent vertebrae and restoration of normal disc height. The spinal implant includes an upper and lower surface adapted to engage cancellous bone tissue in the vertebral bodies. The spinal implant also includes at least two opposing bearing surfaces adapted to bear against cortical bone tissue in the endplates of adjacent vertebrae. This invention also provides an instrumentation to prepare the intervertebral space to receive the spinal implant and techniques for treating patents in need of corrective spinal surgery.

32 Claims, 9 Drawing Sheets

U.S. PATENT DOCUMENTS

| | | | |
|---|---|---|---|
| 5,857,995 A | 1/1999 | Thomas et al. | 604/22 |
| 5,888,224 A | 3/1999 | Beckers et al. | 606/60 |
| 5,888,227 A | 3/1999 | Cottle | 623/17 |
| 5,893,890 A | 4/1999 | Pisharodi | 623/17 |
| 6,080,158 A | 6/2000 | Lin | 606/61 |
| 6,083,225 A | 7/2000 | Winslow et al. | 606/61 |
| 6,159,214 A | 12/2000 | Michelson | 606/80 |

FOREIGN PATENT DOCUMENTS

| | | |
|---|---|---|
| FR | 2724312 | 3/1996 |
| FR | 95 04789 A1 | 3/1996 |
| FR | 2727004 | 5/1996 |
| FR | 94 14068 A1 | 5/1996 |
| FR | 2736538 | 1/1997 |
| FR | 95 08413 A1 | 1/1997 |
| FR | 2 760 355 A1 | 3/1997 |
| FR | 2 724 044 | 6/1997 |
| FR | 2742044 | 6/1997 |
| WO | WO95/08306 | 3/1995 |
| WO | WO96/27348 | 9/1996 |
| WO | WO 97/234174 | 7/1997 |

* cited by examiner

SPINAL IMPLANT AND CUTTING TOOL PREPARATION ACCESSORY FOR MOUNTING THE IMPLANT

CROSS-REFERENCE TO RELATED APPLICATION

This is a continuing-in-part of PCT Application Ser. No. IB98 01 324 filed on Aug. 25 1998, and French Patent Application Number 97 10664 filed on Aug. 26, 1997, both which are hereby incorporated by reference in their entirety.

FIELD OF THE INVENTION

Generally, the present invention relates to spinal implant devices, surgical tools and associated techniques for promoting spinal fusion.

BACKGROUND OF THE INVENTION

It is known that when an intervertebral disc degenerates or is damaged, there is often a compression of the disc and a reduction in the normal intervertebral height. Typically, this condition results in abnormal motions that become a source of pain.

In order to treat pathologies of this type, the disc is often stabilized to eliminate the abnormal motions caused by disc disorders or injuries. Generally, one approach is to prevent articulation between the two vertebrae situated on each side of the damaged disc by bone fusion. This fusion fixes the vertebrae to each other, eliminating the relative mobility causing the pain. Various spinal implants to promote fusion between adjacent vertebrae have been proposed. It has been proposed to interconnect the two vertebrae by a kind of rigid U-shaped stirrup, which restores the discal height with a bone graft material disposed inside the stirrup. However, one drawback of this proposal is its diminishing effectiveness over a period of time.

Another proposal for promoting spinal fusion includes implanting a spinal cage to interconnect the adjacent vertebrae; the spinal cage includes a cylindrical member provided with a series of openings and provided with anchoring points. This implant is placed in a recess formed in the intervertebral disc and penetrates the opposite cortical endplates of the two vertebrae, which were previously hollowed out to receive the implant. This penetration forms openings in the sub-chondral endplates to place spongy bone of the vertebrae in contact with bone graft material placed inside the implant, facilitating bone fusion. U.S. Pat. No. 5,015,247 provides one example of this approach.

Yet another proposal for spinal fusion comprises inserting hollow tubular implants having a generally ovoidal external shape into the intervertebral space. However, these implants require both annular ribs to inhibit axial displacement and longitudinal ribs or teeth to prevent rotation of the implant about its longitudinal axis. One example of this approach is found in U.S. Pat. No. 5,683,463 issued to Godefroy et al. In another example in U.S. Pat. No. 5,888,224 issued to Beckers et al., a rotatable implant for spinal fusion is disclosed. The rotatable implant requires a linking connector to inhibit longitudinal rotation. Other rotatable implants are described in U.S. Pat. No. 5,607,424 issued to Tropiano.

However, one drawback of these proposed implants is their lack of support of the cortical bone tissue, particularly bearing against the peripheral wall of the vertebral bodies. This contributes to their diminishing effectiveness in maintaining normal disc height over a period of time.

Proper performance of a spinal implant of this type requires balancing the need to promote fusion between the spongy bone and the need to form a reliable load bearing relationship with the stronger cortical bone. As a result, the spinal implant must be neither engaged too far into the openings provided in the cortical endplates to provide a sufficiently dense load bearing surface, nor insufficiently inserted, in which case the bone fusion between the two vertebrae would be adversely affected by a poor anchorage. Thus, there is a demand for devices and techniques that facilitate attaining the proper balance between fusion and load support.

Thus, in light of the above described problems, there is a continuing need for advancements in the treatment of spinal deformities, including improved spinal implants and devices relating to spinal fusion and for surgical methods to treat spinal deformities. The present invention is such an advancement and provides a wide variety of benefits and advantages.

SUMMARY OF THE INVENTION

The present invention relates to spinal implants, surgical tools and the use thereof. Various aspects of the invention are novel, nonobvious, and provide various advantages. While the actual nature of the invention covered herein can only be determined with reference to the claims appended hereto, certain forms and features, which are characteristic of the preferred embodiments disclosed herein, are described briefly as follows.

According to one form of the invention, the spinal implant comprises a body having a central part arranged to allow arthrodesis and at least one terminal part for bearing against the cortical bone of the vertebral endplates. The central part is adapted to penetrate the vertebral endplates, transversely projecting from the terminal bearing part. Thus the invention achieves a separation between the end parts constituting the load bearers, and the intermediate part of the implant which permits fusion. In addition, the central part may include at least one cavity for receiving a bone graft material.

In another form of the present invention, an implant for insertion between a first vertebra having a first cortical bone endplate and a second vertebra having a second cortical bone endplate includes two terminal parts. The first terminal part defines a first bearing surface to bear against the first cortical bone endplate and a second bearing surface opposite the first surface to bear against the second cortical bone endplate. The second terminal part opposes the first terminal part and defines a third bearing surface to bear against the first cortical bone endplate and a fourth bearing surface opposite the third surface to bear against the second cortical bone endplate. The implant has an elongated central part defining an upper projection extending past the first and third surfaces, and a lower projection extending past the second and fourth surfaces. These projections correspondingly pass through openings in the first and second cortical bone endplates when the first and third surfaces bear against the first cortical bone endplate and the second and fourth surfaces bear against the second cortical bone endplate. The terminal parts are dimensioned to facilitate restoration of the natural geometry of the intervertebral space (lordosis, kyphosis, and parallel discs). Thus, the first and second surfaces may be separated by a first distance, and the third and fourth surface may be separated by a second distance greater than the first distance to accommodate a natural curvature of the spine.

In a further form of the present invention, an implant with two terminal parts also has an elongated central part that includes a pair of longitudinal walls defining a cavity. The walls define a first edge projecting past the first and third surfaces and a second edge projecting past the second and fourth surfaces. The first and second edges correspondingly penetrate the first and second cortical bone endplates when the first and third surfaces bear against the first cortical bone endplate and the second and fourth surfaces bear against the second cortical bone endplate.

According to another form, the bearing surfaces of the terminal end parts are defined by flanges extending from opposing ends of the implant along its longitudinal axis. Preferably, the bearing surfaces are generally flat for bearing against the cortical bone of the vertebral endplates of the two adjacent vertebrae. It is also preferred that openings be cut into the cortical endplates in their central regions corresponding to the length of a central part of the implant along the longitudinal axis and leaving a region of the cortical bone endplates around the periphery of the openings. The length of the remaining peripheral endplate corresponds to the length of the bearing surfaces along the longitudinal axis. When the implant is placed in position, the edges of the walls of the central part engage the openings cut in the cortical endplates and consequently do not substantially bear against the remaining peripheral portion of the endplates. A cavity may be defined by the central part that holds bone graft material in contact with the spongy bone of the two vertebrae. In contrast, the bearing surfaces of the flanges are disposed adjacent the edges of the openings of the cortical endplates and bear against the remaining portions of the endplates to establish a strong load-bearing relationship. Thus, both bone fusion and support are distinctly accommodated by different parts of the implant structure, which permits obtaining a satisfactory support of the vertebral bodies on the implant and an excellent arthrodesis.

Yet another form of the present invention includes a cutting tool accessory to prepare the cortical endplates of two adjacent vertebrae for insertion of an implant. This tool comprises a proximal handle connected to an elongated shaft configured to rotate about a longitudinal axis of the tool. The tool also includes a first non-cutting portion with the shaft extending therethrough and being configured to rotate relative thereto. A cutting portion is fixed to the shaft to rotate therewith and is positioned distal to the first non-cutting portion. The cutting portion includes a first pair of generally parallel opposing faces and a second pair of opposing faces each extending between the first pair of faces. The second pair of faces each defines a number of cutting teeth. A second non-cutting portion is fixed to the cutting portion that includes a distal head. The first non-cutting portion, the cutting portion, and the second noncutting portion have a rotatably selectable alignment that presents a generally constant height corresponding to the intervertebral space defined between the cortical bone endplates to facilitate insertion therein. Once inserted, the cutting portion may be rotated out of this alignment to cut a first opening in the first cortical bone endplate and a second opening into the second cortical bone endplate. The cutting portion and the non-cutting portions may be arranged to provide uniform, symmetrical cutting of these openings with a predetermined length corresponding to the dimensions of a given implant device.

In an additional form, a technique of spinal fixation includes cutting adjacent vertebrae and inserting an implant therebetween to promote fusion and provide suitable support. The implant may be inserted by anterior or posterior surgical approaches. The cutting may be performed by the cutting tool of the present invention and may include initially inserting the tool so that a first pair of faces are in contact with a respective one of the first and second cortical bone endplates, turning a handle to rotate the cutting portion to remove cortical bone with cutting teeth defined by a second pair of faces, and withdrawing the tool. The tool may be used to form openings readily positioned in the central region of the adjacent vertebrae leaving a portion of the cortical bone endplates about the openings. The insertion of the implant may include positioning the implant of the present invention between the first and second vertebrae and turning the implant about one quarter of a turn.

In another form of the present invention, there is provided an implant for insertion between a first and a second vertebrae, each vertebra having a cortical bone endplate surface. The implant includes a first terminal part that defines a first bearing surface substantially planar and adapted to bear against a first cortical endplate surface and an opposite second bearing surface substantially planar and adapted to bear against a second cortical bone endplate surface; a second terminal part opposite the first terminal part, wherein the second terminal part defines a third bearing surface adapted to bear against the first cortical bone endplate surface and a fourth bearing surface adapted to bear against the second cortical bone endplate surface; and an elongated body extending from the first terminal part to the second terminal part. The implant has an elongated central part that defines a longitudinal axis and has an upper surface arcuate along the longitudinal axis and a lower surface arcuate along the longitudinal axis. In preferred embodiments, the implant includes a cavity for receiving bone osteogenic material to promote bone fusion between adjacent vertebrae. The implant also includes antiexpulsion features such as, for example, at least one ridge transverse to the longitudinal axis. Preferably the implant includes a plurality of ridges proximate to the first and second bearing surfaces to inhibit expulsion of the implant. Furthermore, the second terminal part can be curved to facilitate insertion of the implant into the prepared intervertebral space.

In another form the present invention provides an implant for insertion between a first vertebra and a second vertebra, where the first vertebra has a generally vertically extending first peripheral wall and a first cortical bone endplate and the second vertebra has a generally vertically extending second peripheral wall and a second cortical bone endplate. The implant comprises: A first terminal part defining a first bearing surface adapted to bear against a portion of the cortical bone endplate proximate to the first peripheral wall and an opposite second bearing surface adapted to bear against a portion of the second cortical bone endplate proximate to the second peripheral wall; an elongated body extending from said first terminal part, the body defining a longitudinal axis and having an upper surface and a lower surface, wherein the first upper surface and the second lower surface are arcuate along the longitudinal axis; and a second terminal part opposite the first terminal part and having a insertion face extending from the upper surface to the lower surface wherein the insertion face is provided to ease insertion of the implant between the first vertebra and the second vertebra.

In yet another form of the present invention, there is provided a tool for insertion between a first vertebra having a cortical bone endplate and a second vertebra having a second cortical bone endplate. The insertion tool includes a proximal handle connected to an elongated shaft configured to rotate about a longitudinal axis of the tool; an outer sleeve adjacent to the handle and the shaft extending through the sleeve and configured to rotate relative thereto; a cutting portion fixed to the shaft to rotate therewith, the cutting portion including a pair of generally parallel opposing arms, each arm having a first arcuate cutting edge and an opposite second arcuate cutting edge; and a non-cutting portion fixed to the cutting portion and distal to the handle, wherein the non-cutting portion is configured to align the cutting portion between the first cortical bone endplate of the first vertebra and the second cortical bone endplate of the second vertebra. The insertion tool also can include a stop adapted to bear against the first or second vertebra to limit the depth of insertion of the tool within the intervertebral space. The tool preferably includes a cavity provided between the first and second arms of the cutting portion. The cavity provides a receptacle for receipt of bone debris generated during the scraping procedure. The cutting portion and the non-cutting portion of the tool are adapted to position first and second cutting edges between the first and second vertebrae such that rotation of the cutting head removes substantially equal amounts of bone from the first and second endplates of the adjacent vertebrae.

One object of the present invention is to provide a spinal implant device to promote fusion between adjacent vertebrae. Further objects, features, aspects, forms, advantages and benefits shall become apparent from the description and drawings contained herein.

DETAILED DESCRIPTION OF THE INVENTION

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described processes, systems or devices, and any further applications of the principles of the invention as described herein, are contemplated as would normally occur to one skilled in the art to which the invention relates.

Figure 1:
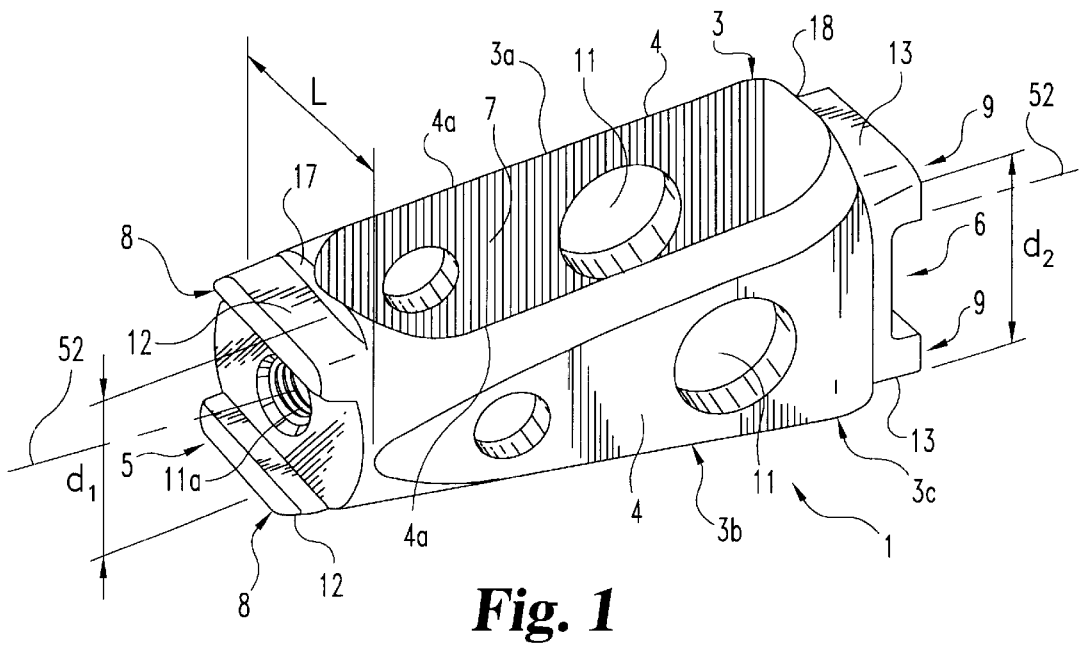
FIG. 1 is a perspective view, to a larger scale, of one embodiment of a spinal implant of the present invention.
Figure 6:
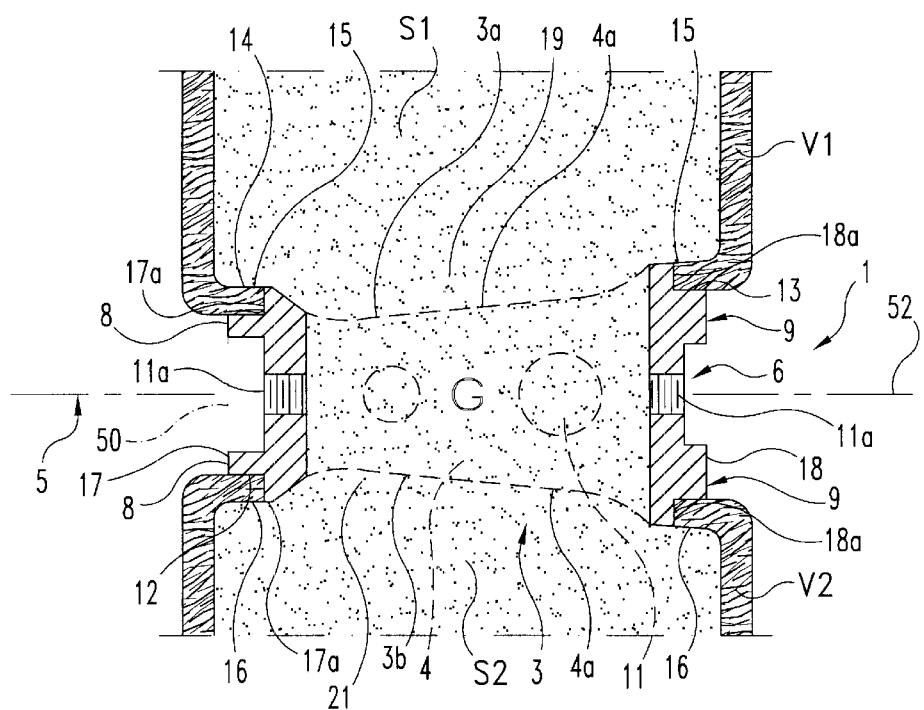
FIG. 6 is a partial sectional view taken in a sagittal plane showing the implant of FIG. 1 positioned in an intervertebral disc for achieving a spinal fusion.
Figure 7:
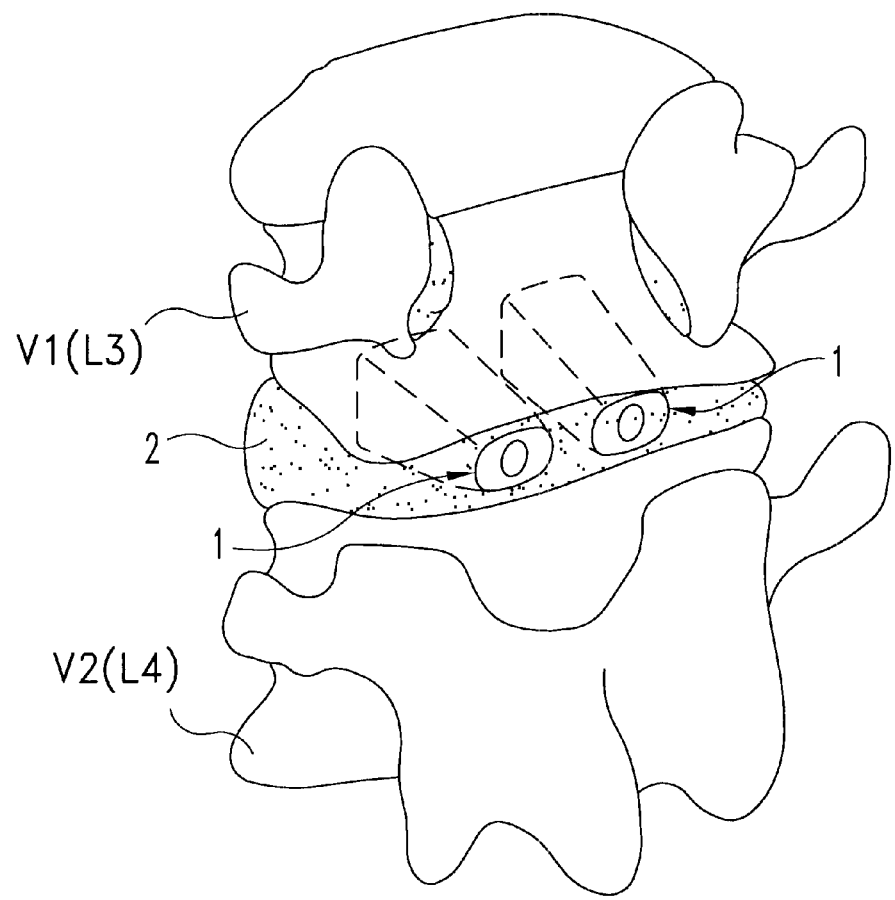
FIG. 7 is a perspective view of a spinal segment in the intervertebral disc in which two implants have been installed.

FIGS. 1, 6, and 7 depict spinal cage implant 1. Implant 1 is adapted to be inserted in a cavity provided in a damaged intervertebral disc 2 (FIG. 7), so as to restore the normal height of the intervertebral space between the two vertebrae V1 and V2 adjacent to the disc 2, for example, the lumbar vertebrae L3, L4 as depicted in FIG. 7. FIG. 1 shows implant 1 disposed along its longitudinal axis 52. Implant 1 comprises a hollow body 3 of elongate shape, having a central part 3c formed by two parallel longitudinal walls 4 arranged to permit the arthrodesis, and, at the two opposite ends of the central part 3c, in the direction of the implantation of the implant 1, two terminal parts 5, 6 for bearing against the cortical bone 14 of vertebral cortical bone endplates 15, 16 of the two vertebrae (V1, V2) adjacent to the disc 2 (see, for example, FIG. 6).

The longitudinal walls 4 define therebetween a cavity 7 and are provided with openings 11. Terminal parts 5, 6 are disposed opposite each other along axis 52 and each includes a terminal face defining a centrally located threaded hole 11a. Holes 11a are configured for engagement by a threaded shaft of an insertion/manipulation accessory (not shown) to facilitate placement of implant 1 between vertebrae V1, V2. The cavity 7 is provided to receive a graft G of spongy bone or any other material favoring bone fusion, for example, a synthetic ceramic.

Terminal part 5 has two opposite bearing surfaces 12 transverse to axis 52 which are so dimensioned that they are separated by distance d1. Terminal part 6 has two opposite bearing surfaces 13 transverse to axis 52 which are so dimensioned that they are separated by distance d2. Distances d1, d2 are adapted to the geometry of the intervertebral space to be restored. When d2 is greater than d1 as depicted, implant 1 is preferred for fusion of vertebrae in a region of the spine having a natural curvature. Distance 1 corresponds to a maximum width dimension of body 3. In one embodiment, the width of body 3 is generally constant along axis 52 and is about the same as distance dl to facilitate a proper fit between vertebrae V1, V2 as will become more apparent hereinafter.

The terminal parts 5, 6 are extended by load-bearing flanges 8, 9, namely, two load bearing flanges 8 for part 5 and two load bearing flanges 9 for part 6. In the depicted embodiment, flanges 8, 9 form parallel bars perpendicular to the longitudinal walls 4, and define generally flat surfaces 12, 13 for bearing against the cortical bone 14 of the vertebral endplates 15, 16.

In the illustrated embodiment, the longitudinal walls 4 have a substantially trapezoidal contour of which the small base corresponds to the terminal part 5 and the large base corresponds to the terminal part 6. The walls 4 constituting the central part 3c of the implant 1 are so shaped as to transversely project from the terminal bearing parts 5, 6, as can be seen in FIGS. 1 and 6. Thus, the walls 4 can penetrate respective openings 19, 21 of the vertebral endplates 15, 16 whose edges bear against the bearing surfaces 12, 13 of the flanges 8, 9 (FIG. 6). Flanges 8, 9 are shaped to define step projections 17a, 18a to further facilitate penetration of openings 19, 21. Projections 17a, 18a also provide a lip to maintain alignment of bearing surfaces 12,13 with cortical bone endplates 15, 16 about the periphery of the openings as shown in FIG. 6. Walls 4 also include tapered edges 4a to facilitate penetration. Correspondingly, central part 3c has upper projection 3a and lower projection 3b defined by edges 4a. Notably, edges 4a and projections 3a, 3b transversely project away from surfaces 12, 13.

Figure 2:
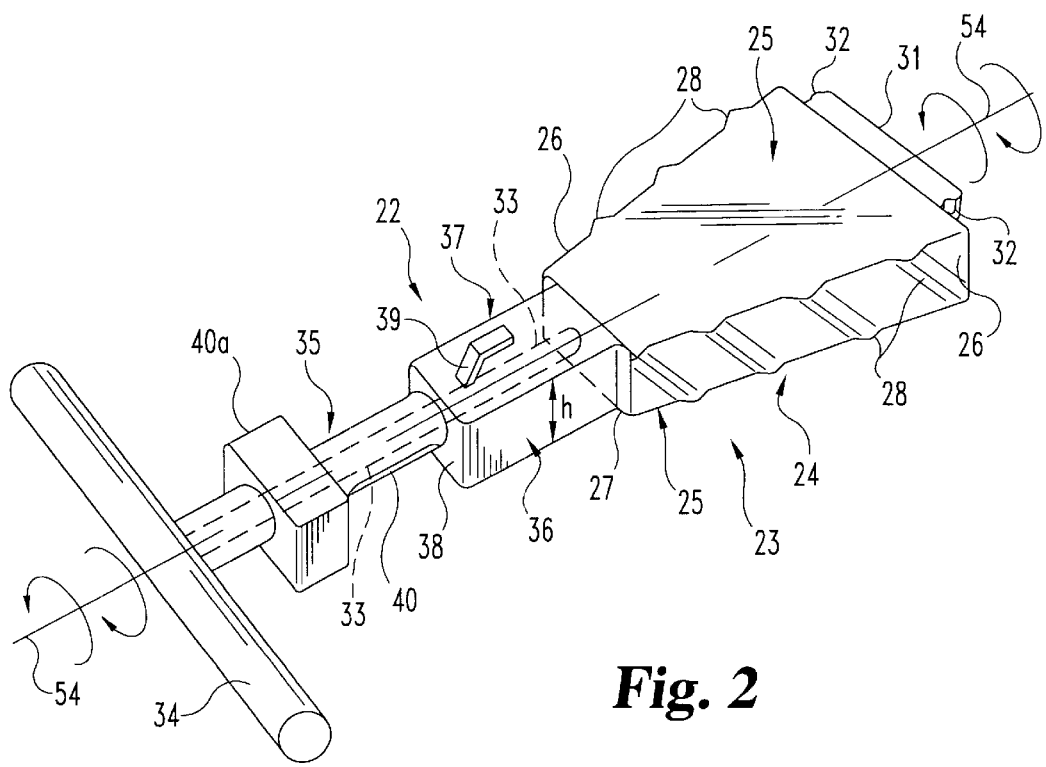
FIG. 2 is a perspective view of one embodiment of a cutting tool of the present invention for mounting the implant of FIG. 1.
Figure 3:
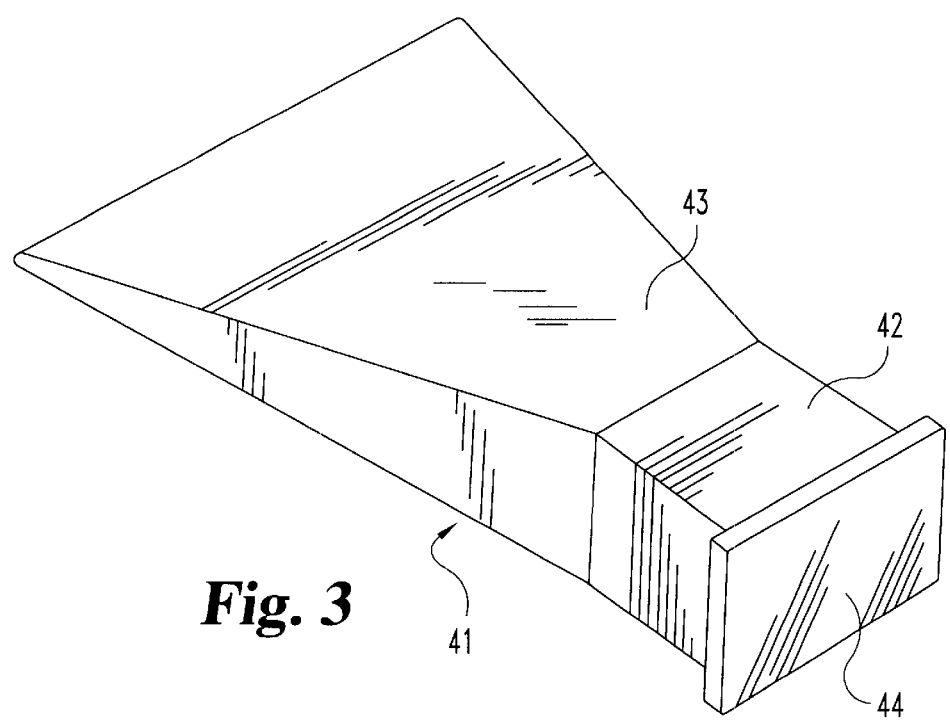
FIG. 3 is a perspective view of a distracting wedge or "distracter" used for carrying out a surgical method in accordance with the present invention.
Figure 4:
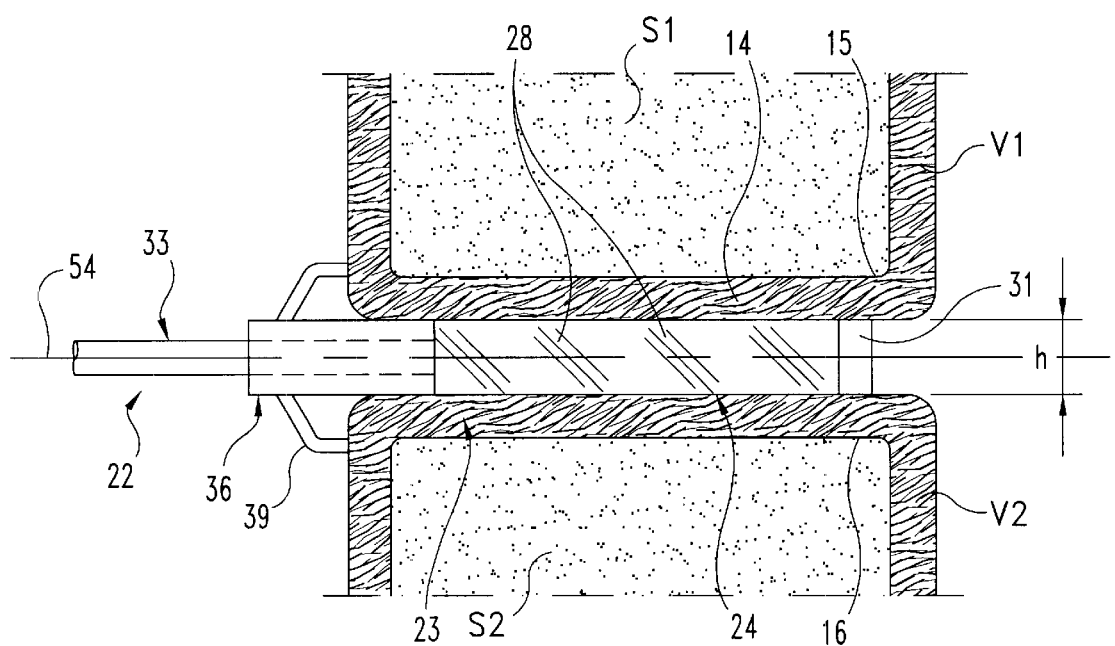
FIG. 4 is a partial elevation view diagrammatically illustrating the insertion of the cutting tool between two vertebrae.
Figure 5:
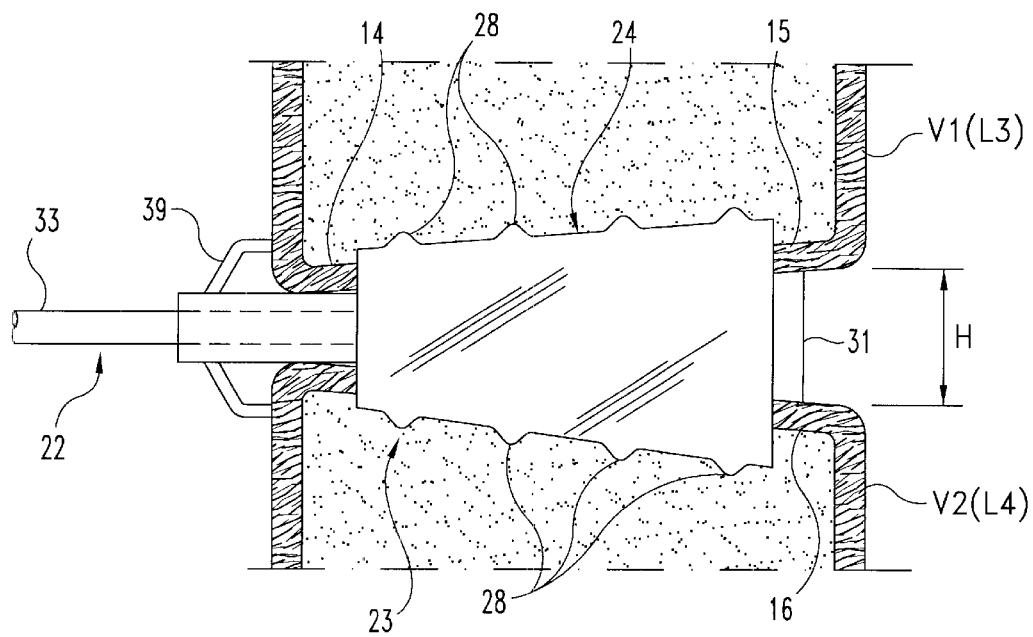
FIG. 5 is a partial elevation view showing the cutting tool after rotation of the cutting portion through 90° and penetrating the cortical endplates of the two adjacent vertebrae.

Implant 1 may be placed in position in the intervertebral disc 2 after preparation with cutting tool accessory 22, which will now be described with reference to FIGS. 2, 4, and 5. Preferably, tool 22 is made from a metallic material suitable for surgical use. Tool 22 has a milling cutter 23 including central cutting portion 24 and two non-cutting portions 31, 36 arranged at opposite ends of central cutting portion 24. Non-cutting portions 31, 36 have a height corresponding to the intervertebral space and permitting uniform, symmetrical cutting of a predetermined length through a central region of both vertebral endplates 15, 16. Preferably, the geometry of portions 24, 31, 36 is determined for preparing the intervertebral space with the geometry of implant 1 to restore the natural lordosis of the intervertebral space; and correspondingly, the distances represented by h and d1 are approximately equal.

Central cutting portion 24 has a trapezoidal shape with two generally smooth, longitudinal faces 25 opposed to each other. Faces 25 are configured to facilitate insertion into the intervertebral space, being generally separated from each other by distance h. Central cutting portion 24 also has cutting faces 26 extending between faces 25. Cutting faces 26 define a number of uniformly spaced-apart cutting teeth 28. Teeth 28 each extend along a generally straight path that is slanted at an oblique angle relative to the longitudinal axis 54 of tool 22. Preferably, central cutting portion 24 is made from a suitable metallic material that has been machined to form teeth 28.

Non-cutting portion 31 is fixed to the distal end of central cutting portion 24. Portion 31 extends from central cutting portion 24 to provide a distal head in the form of a parallelepiped-shaped bar. Portion 31 has a first dimension substantially the same as distance h to be generally coextensive with faces 25 of central cutting portion 24. Portion 31 also has opposing faces 32 separated from each other by a distance H as shown in FIG. 5. Preferably distance H is approximately equal to distance d2 when tool 22 is being utilized to install implant 1.

Tool 22 also includes a shaft or shank 33 connected to a proximal actuating handle 34. Shank 33 is fixed to central cutting portion 24 and non-cutting portion 31. Shank 33 extends from the small end face 27 remote from the non-cutting head 31 and terminates in the handle 34 which permits rotating the cutting portion 24 about the longitudinal axis 54 of tool 22.

Non-cutting portion 36 has a rectangular shape with generally planar faces 37, 38. Portion 36 may be inserted between two consecutive vertebrae during rotation of central cutting portion 24. Portion 36 extends in the direction toward the handle 34 by a tubular part 40 and through block 40a which terminates in the vicinity of the handle 34. Non-cutting portion 36 is provided with lateral stops 39 capable of being put into abutment against the sides of the vertebrae (V1, V2) after insertion therebetween. Non-cutting portion 36 encloses shank 33. Shank 33 is configured to rotate relative to portion 36. Correspondingly, when handle 34 is turned, shank 33, central cutting portion 24, and non-cutting portion 31 rotate together about axis 54 with non-cutting portion 36 preferably remaining stationary. It should be noted that the partial view of FIGS. 4 and 5 does not show handle 34 and depict a cutaway view of non-cutting portion 36 with shank 33 projecting therefrom.

Figure 8:
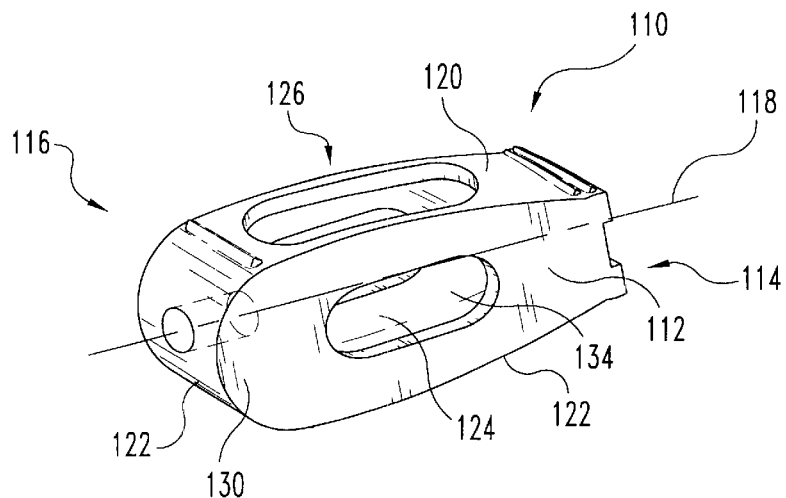
FIG. 8 is a perspective view of an alternative embodiment of a spinal implant according to the present invention.
Figure 9A:
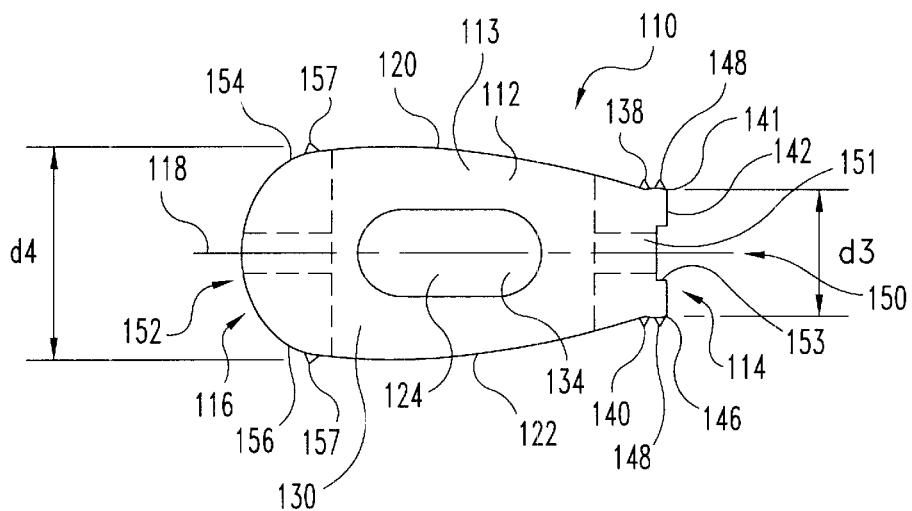
FIG. 9A is an elevated side view of the spinal implant of FIG. 8.
Figure 9B:
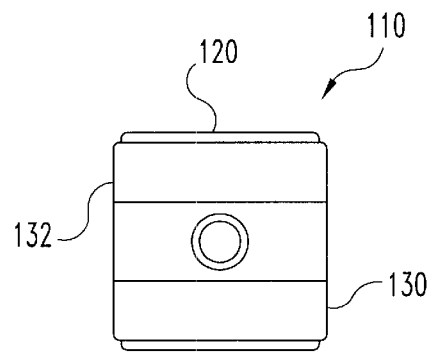
FIG. 9B is an elevated end view of the spinal implant of FIG. 8.

FIGS. 8, 9A and 9B depict an alternative embodiment of a spinal implant of the present invention. Spinal implant 10 is adapted to be inserted into a cavity provided between adjacent vertebrae, for example, between adjacent lumbar vertebrae, to promote fusion of the vertebrae and restore normal disc space height. Implant 110 comprises an elongate body 112 defining a longitudinal axis 118, a first terminal part 114, and a second terminal part 116. At least one of terminal parts 114 and 116, preferably both, includes opposed upper and lower bearing surfaces adapted to bear against cortical bone surfaces of adjacent vertebrae. In one embodiment depicted in FIG. 9B, implant 110 is provided to have a substantially rectangular cross-section when viewed along the longitudinal axis 118.

Elongate body 112 includes central portion 113 that extends from first terminal part 114 to second terminal part 116. Body 112 includes an upper surface 120 and an opposite lower surface 122 defining cavity 124 therebetween. Upper surface 120 and lower surface 122 are adapted to substantially mate with the natural curvature of corresponding facing endplate surfaces of adjacent vertebrae. Thus, the convex curvilinear configuration of upper surface 120 and lower surface 122 facilitates locating the implant approximately in the middle of the vertebra body. As a result, the spinal implant is neither engaged too far into the openings provided in the cortical endplates to provide a sufficiently dense load-bearing surface, nor insufficiently inserted, in which case the bone fusion between the two vertebrae would be adversely affected by a poor anchorage. In another form, upper surface 120 and lower surface 122 are provided as arcuate surfaces along longitudinal axis 118. The arcuate surfaces inhibit expulsion, particularly posterior expulsion, of the surgically implanted spinal implant by providing an implant that has a maximum height that is greater than the height of the surgically prepared entrance in the posterior vertebrae body walls into the intervertebral space.

Further, upper bearing surface 120 includes at least one opening 126 extending into cavity 124. Similarly, lower bearing surface 122 includes at least one opening (not shown) into cavity 124. The perimeter of both the upper and lower bearing surfaces is substantially continuous and uninterrupted. Cavity 124 is provided to receive a graft of osteogenetic material, such as spongy bone or other material favoring bone growth, including synthetic bone media. Therefore, the curvilinear configuration of upper surface 120 and lower surface 122 and their associated openings 126 allow interpenetration of the cancellous bone revealed in the surgically prepared intervertebral space of adjacent vertebrae. Interpenetration of the cancellous bone of the vertebra enhances the intimate contact and interdiffusion of osteogenic material initially deposited in cavity 124 with the cancellous bone tissue and greatly enhances the potential for bone growth.

Elongate body 112 can also include sidewalls 130 and 132 extending from upper surface 120 to lower surface 122. Sidewalls 130 and 132 can include openings 134 providing communication into cavity 124 to further enhance interdiffusion of the osteogenic material in cavity 124 with cancellous bone tissue.

Referring to FIG. 9B, in one embodiment upper surface 120 and lower surface 122 have a substantially uniform height from sidewall 130 to sidewall 132 in a direction transverse to longitudinal axis 118.

First terminal part 114 includes a first bearing surface 138, an opposite second bearing surface 140, and a terminal face 142 extending therebetween. Preferably first bearing surface 138 and second bearing surface 140 include substantially planar surfaces 141 and 146, respectively, adapted to engage surfaces of cortical bone endplates on adjacent vertebral bodies. When inserted within the prepared intervertebral space, first bearing surface 138 and second bearing surface 140 bear against cortical bone tissue proximate to the posterior wall of the vertebral bodies. The implants can sustain the compressive forces associated with normal activity and resist receding into the spongelike cancellous bone tissue of the vertebral body. The desired disc height can be maintained for an extended time period while bone fusion progresses. First bearing surface 138 and second bearing surface 140 are separated by a distance d3 selected to restore normal disc space height and natural lordosis. Further, in a preferred aspect, first bearing surface 130 and second bearing surface 140 are substantially planar surfaces extending substantially parallel to longitudinal axis 118. It will be appreciated that implant 110 can be adapted to be inserted in intervertebral spaces of vertebrae other than lumbar vertebrae. Therefore, distance d3 can be varied to accommodate varying disc heights and natural lordosis.

In preferred embodiments, first and/or second bearing surface 138 and 140 include anti-expulsion features 148, for example, ridges, teeth, and other projections, adapted to inhibit the expulsion of implant 110 from the intervertebral space. In one embodiment, the anti-expulsion surface features include a ridge transverse to longitudinal axis 118. In a preferred form, the anti-expulsion features are adapted to minimize the force needed to insert implant 110 into prepared intervertebral space, yet inhibit expulsion of implant 110. Examples of such preferred forms include ratchet-shaped ridges or teeth that have an apex pointing toward the first terminal end. When thus configured, the ratchet-shaped ridges or teeth chisel deeper into the cortical bone tissue in response to a posteriorly directed expulsive force.

Terminal face 142 includes tool-engaging portion 150. Tool-engaging portion 150 can be provided with a variety of features adapted to engage an insertion tool for insertion of implant 110 into the intervertebral space. For example, tool-engaging portion 150 can include a variety of indents and openings, which may or may not be threaded, to engage correspondingly configured features on an insertion, manipulation accessory (not shown) to facilitate implantation and/or rotation of implant 110 in the intervertebral space. In the preferred embodiment of FIGS. 8 and 9, tool-engaging portion 150 includes a longitudinally extending threaded bore 151 and a driving indent 153.

Second terminal part 116 is opposite first terminal part 114. Second terminal part 116 can include third bearing surface 154, opposing fourth bearing surface 156, and an insertion face 152 extending therebetween. Third bearing surface 154 and fourth bearing surface 156 are adapted to bear against surfaces of cortical bone endplates proximal to the anterior wall of adjacent vertebral bodies. In preferred forms, third bearing surface 154 and fourth bearing surface 156 are provided as curved surfaces that can abut correspondingly curved surfaces of cortical bone prepared using a cutting/insertion tool (described below). Third and fourth bearing surfaces 154 and 156, respectively, are separated by a distance, d4. In the preferred illustrated embodiment, distance d4 is selected to be greater than d3 to restore desired anterior disc height of vertebrae, V1 and V2 and maintain a desired angulation between the vertebrae. While third and fourth bearing surfaces 154 and 156 are shown as curved surfaces, it is understood that these bearing surfaces can be provided in a variety of shapes including convex or ogival in either the horizontal or vertical plane or both, or substantially planar as depicted for the first and second bearing surfaces 138 and 140, respectively.

Further, third and fourth bearing surfaces 154 and 156 can include anti-expulsion features 157 as described for first and second bearing surfaces 138 and 140. The antiexpulsion features are preferably provided in a configuration to ease insertion of implant 110 into the prepared intervertebral space while inhibiting expulsion of the implant.

Second terminal part 116 includes insertion face 152 extending between upper surface 120 and lower surface 122. Insertion face 152 is adapted to minimize the force needed to insert spinal implant 110 into a prepared cavity in the intervertebral space between adjacent vertebrae. In one form, insertion face 152 is provided as a curved surface. In alternative configurations, insertion face 152 can be provided as a convex surface. Further, insertion face 152 can include one or more openings providing communication with cavity 124 of body 112 to facilitate interdiffusion of osteogenic material with bony tissue and thus promote bone growth of adjacent vertebrae V1 and V2.

Preferably implant 110 is made as a single, integral piece. Implant 110 is made of physiologically acceptable material having the requisite strength to withstand the compressive force exerted on the spinal column during normal activity. Examples of such acceptable material include titanium, composites, ceramics, bone, stainless steel and surgical steel.

Figure 10:
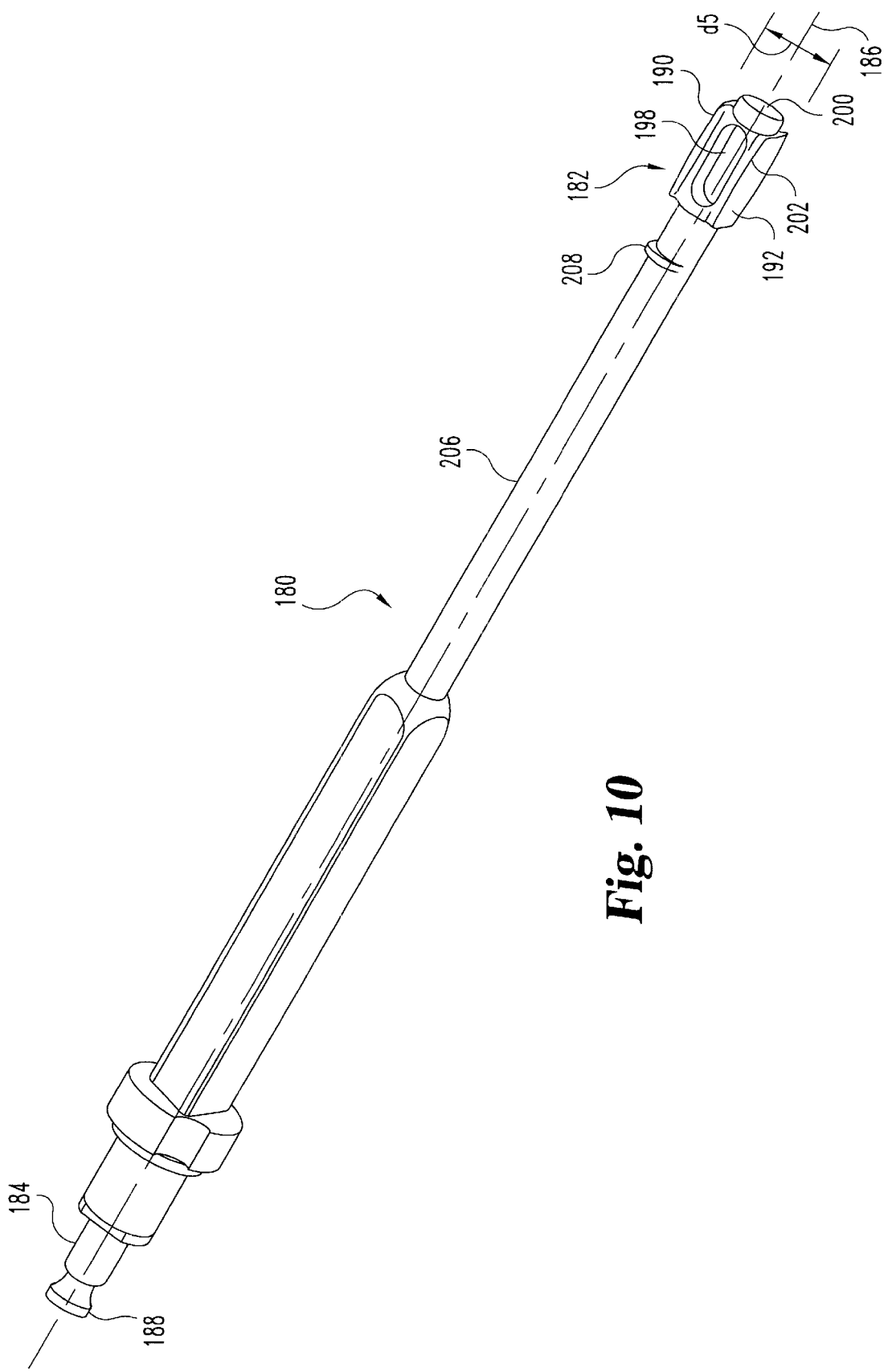
FIG. 10 is a perspective view of an alternative embodiment of a cutting tool for use with the present invention.
Figure 11:
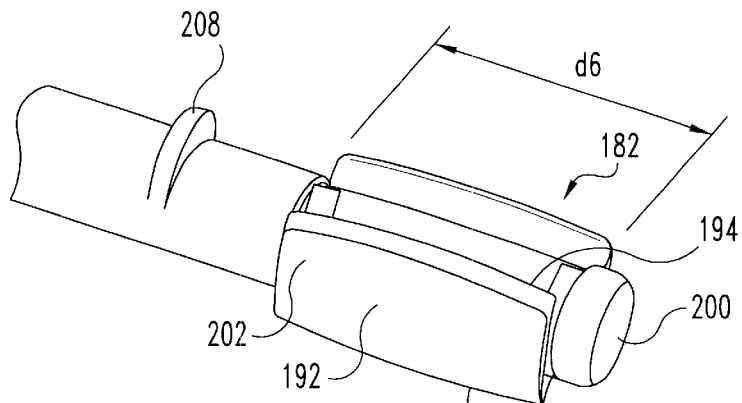
FIG. 11 is a partial view illustrating the cutting head of the cutting tool of FIG. 10.

Implant 110 may be inserted into an intervertebral space after preparation of the endplate of adjacent vertebrae using cutting tool 180, which will now be described with reference to FIGS. 10–12. Cutting tool 180 includes a cutting head 182, shaft 184 defining a longitudinal axis 186, and handle-engaging portion 188.

Cutting head 182 is attached to the distal end of shaft 184. Cutting head 182 includes a first arm 190 and a second arm 192 extending generally parallel to longitudinal axis 186. Opposed first arm 190 and second arm 192 include two generally smooth, longitudinal faces 202 and 204. Faces 202 and 204 are configured to facilitate insertion of cutting head 182 into the intervertebral space, and are generally separated from each other by a distance d5.

First and second arms 190 and 192 each include first arcuate cutting edge 194 and a second opposite arcuate edge 196. Thus, cutting head 182 includes a total of four cutting edges. First cutting and second cutting edges 194 and 196, respectively, are provided in a configuration to substantially conform to arcuate upper and lower surfaces of implant 110. Further, first and second arms 190 and 192 and their included first and second cutting edges 194 and 196 are adapted to cut and remove a portion of cortical bone tissue on opposing endplates of adjacent vertebrae V1 and V2, while substantially retaining the natural concave curvature of the endplates. The cutting edges 194 and 196 have a length d6 selected to avoid cutting the anterior and posterior portions of the endplates and the vertebral wall of vertebrae selected for treatment. The cavity thus prepared with cutting tool 180 provides contact with the graft material in implant 110 and the spongy bone of the two vertebrae. The bearing surfaces of implant 110 are disposed adjacent the edges of the openings of the cortical endplates and bear against the remaining portions of the endplates to establish a strong load bearing relationship.

First arm 190 and second arm 192 are generally opposed and define a cavity 198 therebetween for receipt of bony debris generated during the cutting operation. The bony debris collected from the cutting operation can be saved and packed in the cavity 124 of implant 110 to promote vertebral fusion. Proximal end of first arm 190 and second arm 192 attach to the distal terminus of shaft 184. Opposite ends of first arm 190 and second arm 192 attach to non-cutting portion 200.

Non-cutting portion 200 of cutting head 182 is fixed to the distal end of first arm 190 and second arm 192. Preferably, non-cutting portion 200 has a first dimension transverse to the longitudinal axis substantially the same as distance d5 to be generally co-extensive with faces 202 and 204 of arms 194 and 196. Non-cutting portion 200 also is adapted to align faces 202 and 204 an equal distance from opposed endplate surfaces of adjacent vertebrae to facilitate removal of equal amounts of cortical bone tissue from adjacent vertebrae. Further, non-cutting portion 200 is adapted to inhibit removal of cortical bone from the anterior cortical bone surfaces of adjacent vertebrae. While the non-cutting portion is depicted as a cylindrical abutment, it is understood that alternative configurations are also included within this invention. Such alternative configurations include spherical, semispherical, frustoconical and the like.

Shaft 184 is rotatably received within sleeve 206. Sleeve 206 includes stop 208 adapted to bear against a vertebral body when the cutting edge is inserted into the intervertebral space. Preferably, stop 208 is adapted to inhibit interference with the interspinal processes and associated nerve bodies. In one embodiment, stop 208 is adapted to engage a single vertebral body.

Handle-engaging portion 188 is attached to the proximate end of shaft 184. Handle-engaging portion 188 is adapted to releasably engage a variety of handles known in the art (not shown) to facilitate rotation of shaft 184 and cutting head 182. Alternatively, it is understood that cutting tool 180 can include a handle fixedly attached to the proximal end of shaft 184.

Figure 12:
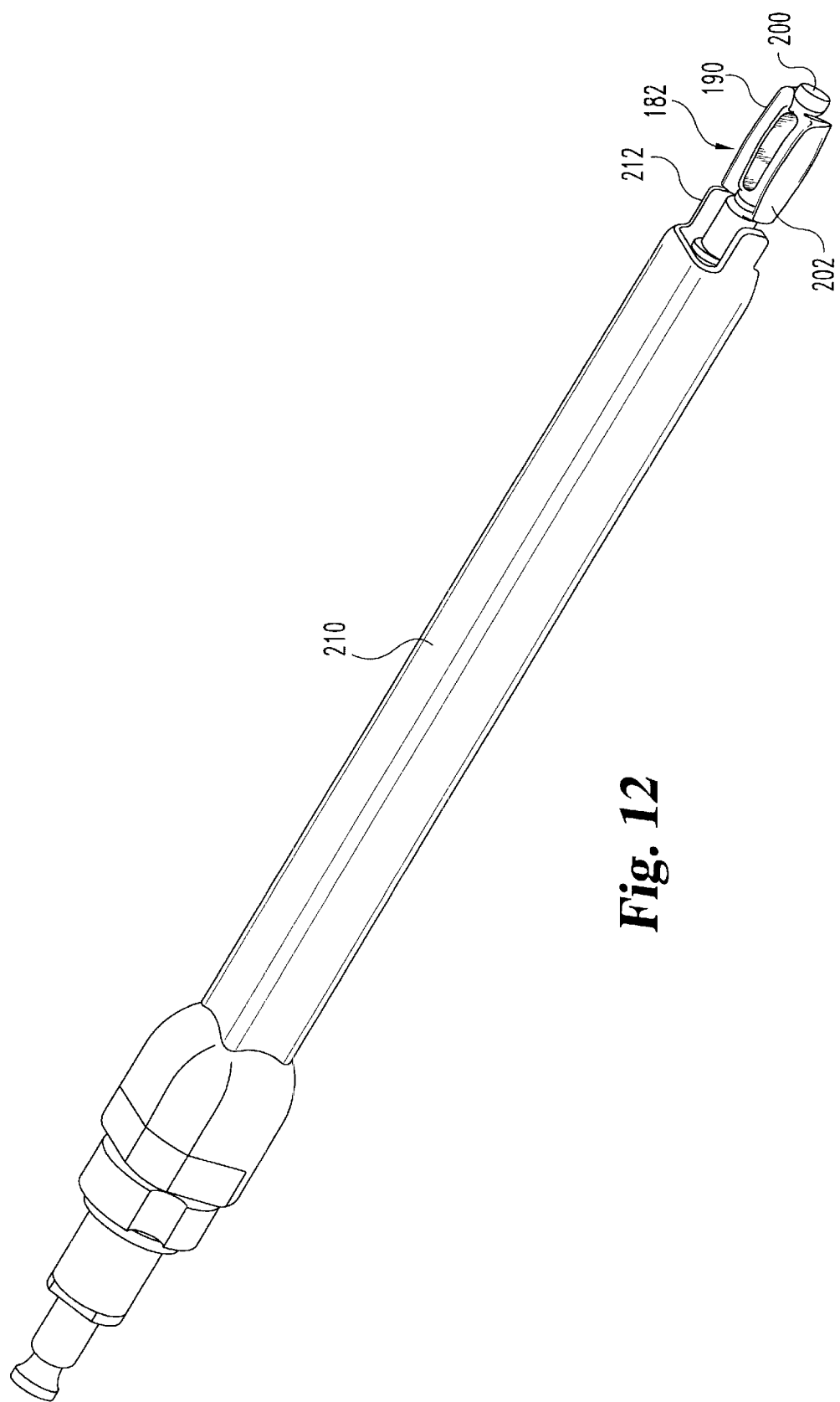
FIG. 12 is a perspective view of one embodiment of the cutting tool of FIG. 10 received within a guide sleeve.

Cutting tool 180 can be provided for use in conjunction with guide sleeve 210 illustrated in FIG. 12. When used with a guide sleeve, cutting tool 180 can be slideably received within the guide sleeve to protect nerve tissue and related spinal processes and orientated with respect to the disc space. A variety of guide sleeves suitable for use with this invention are known and commonly used in surgical procedures. Guide sleeve 206 can include a variety of structural features adapted to facilitate distraction of the vertebrae and fixation of the selected vertebrae and associated instruments for performing spinal surgery. Such structural features can include, for example, insertion fins 212, pins (not shown) and clamps (not shown).

The implant and associated surgical instruments described and/or disclosed in this application can be provided as a surgical kit. The surgical kit can include a number of implants as described herein including implants having varying dimensions for use with patents of varying ages and sizes, and for implantation adjacent to different vertebrae of the spine. The associated surgical instruments including the cutting tool, distracters and guide sleeve are configured and sized to facilitate the implantation of the varying sized implants.

Various non-limiting embodiments of a spinal fixation or fusion procedure of the present invention are next described. One procedure is characterized by: (a) Cutting the vertebrae V1 and V2 and disc 2 with tool 180 to prepare for implantation of implant 110, and (b) Inserting implant 110 between vertebral bodies V1' and V2'. Another more detailed procedure for fusing two vertebrae together is described in terms of the procedural stages A–H as follows:

(A) The surgeon reveals the vertebrae in need of fusion using known surgical techniques. The surgeon then separates the dural sleeve forming an extension of the bone marrow if the procedure is in the lumbar region and then carries out a discectomy to provide a space for implant 110 in the disc space.

(B) The surgeon inserts between the two vertebral bodies V1, V2 from the rear (posterior), two distracters known in the art. Distracters may be inserted laterally with respect to the cavity provided by the discectomy and then turned 90° so as to spread apart the vertebral bodies and to restore disc height. If a lordotic angle is intended, the distracters may include tapered surfaces intended to establish the desired angulation. Next, one of the distracters is removed.

Figure 13:
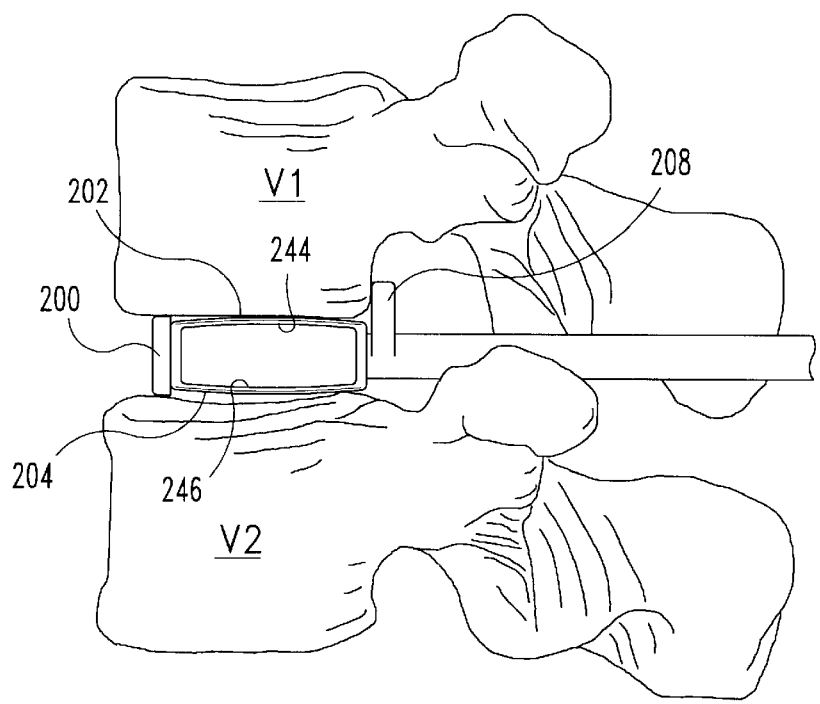
FIG. 13 is an elevated side view in partial section of one embodiment of a cutting tool of FIG. 10 received within the intervertebral space of adjacent vertebrae V1 and V2.
Figure 14:
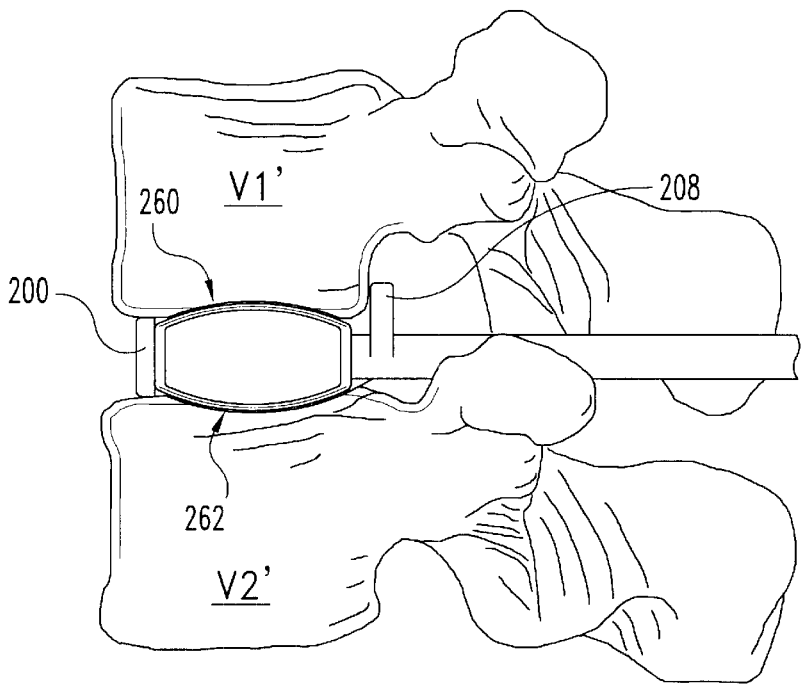
FIG. 14 is an elevated side view in partial section of the cutting tool of FIG. 10 rotated 90 degrees within the intervertebral space of adjacent vertebrae V1' and V2'.

(C) The surgeon then inserts cutting tool 180 between vertebral bodies V1 and V2 so that the faces 202 and 204 are in contact with the vertebral endplates as shown in FIG. 13. When the cutting head 182 is correctly positioned in the central region of the cortical endplates, stop 208 abuts the outer surface of V1 or V2, and non-cutting portion 200 is proximal to the interior cortical bone wall of V1 and V2.

(D) Next, the surgeon rotates handle 188, causing cutting head 182 to rotate about longitudinal axis 186. Typically, the surgeon rotates handle 188 through only a partial rotation to engage cutting edges 194 and 196 with the cortical bone of the adjacent endplates and then changes direction to generate an oscillating cutting action. Cutting action continues until the proper amount of vertebral endplate is removed. When non-cutting portion 200 is correctly positioned between interior cortical bone portions of adjacent vertebrae V1 and V2, first cutting edge 194 and second cutting edge 196 cut equally through endplates 244 and 246. Remaining portions of endplates 246 and 248 bear against non-cutting portion 200 and non-rotating shaft 206. Bony debris generated by the cutting of cortical bone is received in cavity 198 between first arm 190 and second arm 192.

(E) Then, the surgeon withdraws cutting tool 180 from the intervertebral space. Bony debris residing in cavity 198 can then be collected and packed inside cavity 124 of implant 110.

Figure 15:
FIG. 15 is a perspective view in partial section of one embodiment of a spinal implant received within the intervertebral space of adjacent vertebrae V1' and V2'.

(F) The surgeon then implants implant 110, previously filled with either osteogenic material or bony debris, between endplates 244 and 246 from the posterior of vertebral bodies V1 and V2. Implant 110 is positioned such that arcuate upper surface 120 and lower surface 122 engage cut portions of endplate 244 and 246, while remaining uncut portions of endplates 244 and 246 bear against bearing surfaces 138 and 140. In addition, bearing surfaces 154 and 156 on the second terminal portion of implant 110 contact the non-cut interior cortical bone surfaces of adjacent vertebrae. Implant 110 may be presented flat, so that sidewalls 134 and 136 contact cut portions of endplates 244 and 246. Thereafter, the surgeon turns implant 110 through a quarter of a turn about its longitudinal axis 118 so as to place it in the position with walls 134 and 136 perpendicular to the cortical endplates and its arcuate upper surface 120 and lower surface 122 in contact with the cut portion of endplates 260 and 262 as shown in FIG. 15. When implant 110 is in its final position, in which it is stabilized, a bone graft or other osteogenic material is in contact with the spongy portion, promoting bone fusion.

Figure 16:
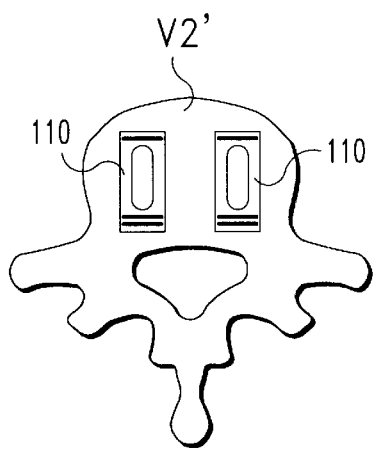
FIG. 16 is a top elevated view of two implants depicted in FIG. 8 positioned on an endplate of a vertebral body.

(G) The surgeon then removes the second distracter and repeats the preceding sequences of stages (A) through (G) to mount a second spinal implant 110 by placing it in position generally parallel to the first spinal implant 110 as illustrated in FIG. 16.

In other embodiments, it is envisioned that the described stages may be altered, deleted, combined, repeated, or re-sequenced, as would occur to those skilled in the art. By way of a non-limiting example, the procedure according to the present invention may utilize one or more different tools to prepare the spine for fixation by the implantation of the present invention. In another example, the tools of the present invention may be utilized to prepare a surgical site for an implant.

The scope of the invention is not intended to be limited to the ascribed embodiment and may also include variants within the scope of the accompanying claims. For example, bearing surfaces 138, 140, 154, and 156 may have any shape, such as curved or cylindrical shaped, with endplates 244 and 246 being correspondingly cut to allow placing the bearing surface in a suitable position. Further, these bearing surfaces may be interconnected in pairs to constitute a single member. Further, the bearing surfaces may also include a variety of structural features adapted to inhibit expulsion of implant 110 from the intervertebral space.

Likewise, the body 112 of implant 110 may include any shape, preferably retaining edges that project from the endplate contacting portions. In particular, the body may have a multitude of cells residing within the interior cavity 124. Also, it should be generally noted that the implant 110 and tool 180 of the present invention can be adapted to a geometry of the spine with respect to lordosis, kyphosis, or parallel vertebral endplates. Thus, the present invention includes application to adjacent vertebrae other than the lumbar vertebrae. Correspondingly, the implant and the cutting portion of the tool may have a different shape, such as a cylindrical geometry, other than the general teardrop geometry depicted. Also, instead of using the disclosed implant 110, the spinal space prepared by tool 180 can be filled with any other material as would occur to those skilled in the art.

According to other embodiments, the implants described herein can be partly or totally constituted by porous rehabitable or other resorbable materials favoring osteointegration. Such embodiments include: (a) an implant according to the above-illustrated geometry made entirely of a resorbable or rehabitable material; (b) an implant in which the whole of the central part is made of a resorbable or rehabitable material; or (c) an implant in which the periphery of the central part is of a metallic or other material and the inside part is of a material favoring osteointegration that may be in an initially solid, pasty, or liquid state. Preferably, the implant 110 of the present invention is provided in a biocompatible metal, such as titanium or surgical steel.

The present invention contemplates modifications as would occur to those skilled in the art. It is also contemplated that processes embodied in the present invention can be altered, rearranged, substituted, deleted, duplicated, combined, or added to other processes as would occur to those skilled in the art without departing from the spirit of the present invention. In addition, the various stages, steps, procedures, techniques, phases, and operations within these processes may be altered, rearranged, substituted, deleted, duplicated, or combined as would occur to those skilled in the art. All publications, patents, and patent applications cited in this specification are herein incorporated by reference as if each individual publication, patent, or patent application was specifically and individually indicated to be incorporated by reference and set forth in its entirety herein.

While the invention has been illustrated and described in detail in the drawings and foregoing description, the same is considered to be illustrative and not restrictive in character, it is understood that only the preferred embodiments have been shown and described and that all changes and modifications that come within the spirit of the invention are desired to be protected.

What is claimed is:

1. An implant for insertion between a first vertebra and a second vertebra, the first vertebra having a first cortical bone endplate and the second vertebra having a second cortical bone endplate, wherein the implant comprises:
    a first terminal part defining a first bearing surface substantially planar and adapted to bear against the first cortical bone endplate and an opposite second bearing surface substantially planar and adapted to bear against the second cortical bone endplate;
    a second terminal part opposite said first terminal part, said second terminal part defining a third bearing surface adapted to bear against the first cortical bone endplate, a fourth bearing surface adapted to bear against the second cortical bone endplate, and an insertion face extending arcuately from the third bearing surface to the fourth bearing surface, said third bearing surface and said fourth bearing surface include an anti-expulsion feature; and
    an elongated body including a central portion extending from said first terminal part to said second terminal part, said body defining a longitudinal axis and having an upper bearing surface and a lower bearing surface, wherein the upper bearing surface and the second lower bearing surface are arcuate along the longitudinal axis.

2. The implant of claim 1 wherein the body defines a cavity for receiving bone osteogenic material.

3. The implant of claim 2 wherein the upper bearing surface and the lower bearing surface each include at least one opening into the cavity and a continuous perimeter surface.

4. The implant of claim 1 wherein the first bearing surface and the second bearing surface include an anti-expulsion feature.

5. The implant of claim 4 wherein the anti-expulsion feature includes ridges transverse to the longitudinal axis.

6. The implant of claim 1 wherein the third and fourth bearing surfaces are curved.

7. The implant of claim 1 wherein the upper bearing surface and the lower bearing surface are adapted to engage a cancellous bone portion of the first and second vertebrae.

8. The implant of claim 1 wherein the upper bearing surface is configured to mate with the first cortical bone endplate and the lower bearing surface is configured to mate with the second cortical bone endplate.

9. The implant of claim 1 wherein first bearing surface and the second bearing surface are separated by a first distance, and the third bearing surface and the fourth bearing surface are separated by a second distance greater than the first distance.

10. The implant of claim 1 wherein the upper bearing surface is configured to mate with the first cortical bone endplate and the lower bearing surface is configured to mate with the second cortical bone endplate.

11. The implant of claim 1, said implant composed of a composite material.

12. An implant for insertion between a first vertebra and a second vertebra, the first vertebra having a generally vertically extending first peripheral wall and a first cortical bone endplate and the second vertebra having a having a generally vertically extending second peripheral wall and a second cortical bone endplate, wherein the implant comprises:

a first terminal part defining a first bearing surface adapted to bear against a portion of the cortical bone endplate proximate to the first peripheral wall and an opposite second bearing surface adapted to bear against a portion of the second cortical bone endplate proximate to the second peripheral wall, an elongated body including a central part extending from said first terminal part, said central part defining a longitudinal axis and having an upper bearing surface and a lower bearing surface wherein the upper bearing surface and the lower bearing surface extend arcuately from the first terminal part in a direction substantially parallel to the longitudinal axis, terminating in a second terminal part opposite, said first terminal part, said second terminal part including an anti-expulsion feature and having an insertion face extending from the first upper bearing surface to the second lower bearing surface wherein said insertion face consists of a curved surface, said curve extending from the upper bearing surface to the lower bearing surface.

13. The implant of claim 12 wherein the body defines a cavity for receiving bone osteogenic material.

14. The implant of claim 12 wherein the first bearing surface and the second bearing surface include at least one anti-expulsion feature.

15. The implant of claim 14 (wherein the anti-expulsion feature includes a ridge transverse to the longitudinal axis.

16. The implant of claim 12 wherein the first bearing surface and the second bearing surface are substantially planar.

17. The implant of claim 12 wherein the second terminal part includes a third bearing surface provided to bear against a portion of the cortical bone endplate proximate to the first peripheral wall and an opposite fourth bearing surface adapted to bear against a portion of the second cortical bone endplate proximate to the second peripheral wall.

18. The implant of claim 17 wherein the third bearing surface and the fourth bearing, surface include anti-expulsion features.

19. The implant of claim 17 wherein the third and fourth bearing surface are curved.

20. The implant of claim 12 wherein the upper bearing surface and the lower bearing surface include openings into the cavity.

21. The implant of claim 12 wherein the upper bearing surface and the lower bearing surface are adapted to engage cancellous bone of the first and second vertebrae.

22. The implant of claim 12, said implant formed of a composite material.

23. An implant for promoting spinal fusion between adjacent vertebrae, said implant comprising an elongate body having a cavity therein and defining a longitudinal axis therethrough, said body comprising:

an upper surface extending arcuately in a direction substantially parallel to the longitudinal axis, said upper surface comprising an opening into the cavity;

an opposite lower surface extending arcuately in a direction substantially parallel to the longitudinal axis, said lower surface comprising an opening into the cavity;

a first terminal end extending from the upper surface to the lower surface and having a rectangular cross-section transverse to the longitudinal axis;

an opposite second terminal end extending convexly from the upper surface to the lower surface and including an anti-expulsion feature projecting therefrom; and, an osteogenic material disposed within the cavity.

24. The implant of claim 23 comprising a first lateral wall and an opposite second lateral wall, said first and second lateral walls extending from the upper surface to the lower surface and each wall having an opening into the cavity.

25. The implant of claim 24 wherein the first terminal end comprises a ridge extending from the first lateral wall to the second lateral wall.

26. The implant of claim 25 wherein the anti-expulsion feature extending from the second terminal end comprises a ridge extending from the first lateral wall to the second lateral wall.

27. The implant of claim 23 wherein the first terminal end comprises a tool-engaging portion.

28. The implant of claim 23 wherein the tool-engaging portion comprises a slot.

29. The implant of claim 23 wherein the tool-engaging portion comprises a bore.

30. The implant of claim of 23 wherein the second terminal end comprises an opening into the cavity.

31. The implant of claim 23 wherein said body is composed of a composite material.

32. The implant of claim 23, wherein said body is composed of a biocompatible metal.

* * * * *

UNITED STATES PATENT AND TRADEMARK OFFICE
CERTIFICATE OF CORRECTION

PATENT NO.    : 6,610,089 B1                                                   Page 1 of 1
DATED         : August 26, 2003
INVENTOR(S)   : Liu et al.

It is certified that error appears in the above-identified patent and that said Letters Patent is hereby corrected as shown below:

<u>Column 15,</u>
Line 15, please change "having a having a" to -- having a --.
Line 34, please delete the comma after the word "opposite".
Line 34, please delete the hard-return after the word "opposite" so that the paragraph beginning "said first terminal part, said second…" immediately follows the word "opposite".
Line 47, please change "(wherein the anti-expulsion" to -- wherein the anti-expulsion --.

Signed and Sealed this

Sixth Day of January, 2004

JAMES E. ROGAN
*Director of the United States Patent and Trademark Office*